US011642117B2

(12) United States Patent
Nguyen et al.

(10) Patent No.: US 11,642,117 B2
(45) Date of Patent: May 9, 2023

(54) LIGAMENT RETRACTOR

(71) Applicant: Optimotion Implants LLC, Orlando, FL (US)

(72) Inventors: Vuong Binh Nguyen, Windermere, FL (US); Daniel F. Justin, Orlando, FL (US)

(73) Assignee: NGUYEN PARTNERSHIP, LLLP, Windermere, FL (US)

( * ) Notice: Subject to any disclaimer, the term of this patent is extended or adjusted under 35 U.S.C. 154(b) by 472 days.

(21) Appl. No.: 16/803,501

(22) Filed: Feb. 27, 2020

(65) Prior Publication Data

US 2020/0275917 A1    Sep. 3, 2020

Related U.S. Application Data

(60) Provisional application No. 62/812,245, filed on Feb. 28, 2019.

(51) Int. Cl.
*A61B 17/02* (2006.01)
*A61B 17/17* (2006.01)

(52) U.S. Cl.
CPC ...... *A61B 17/0206* (2013.01); *A61B 17/1764* (2013.01)

(58) Field of Classification Search
CPC ... A61B 17/02; A61B 17/0206; A61B 17/142; A61B 17/157; A61B 17/1764; A61B 2017/00477; A61B 2090/08021
See application file for complete search history.

(56) References Cited

U.S. PATENT DOCUMENTS

| 3,776,240 | A |   | 12/1973 | Woodson |
|---|---|---|---|---|
| 4,520,797 | A | * | 6/1985 | Petersen ............... A61B 17/02 606/198 |
| 5,334,194 | A | * | 8/1994 | Mikhail ............... A61B 17/025 606/88 |
| 5,380,331 | A |   | 1/1995 | Mikhail |

(Continued)

FOREIGN PATENT DOCUMENTS

| CN | 105380704 A | 3/2016 |
|---|---|---|
| CN | 110859648 A | 3/2020 |

(Continued)

OTHER PUBLICATIONS

International Search Report and Written Opinion dated Jun. 11, 2020 received in corresponding International Application No. PCT/US2020/020142.

*Primary Examiner* — Nicholas J Plionis
(74) *Attorney, Agent, or Firm* — David Meibos; Maywood IP Law

(57) ABSTRACT

An assembly may include a retractor pivotally coupled to a guide rod. The retractor may include a generally arcuate projection having a convex retractor surface, a concave cutting shield surface, and a retractor coupling feature. The guide rod may include an elongate member and a rod coupling feature that may be configured to engage the retractor coupling feature to pivotably couple the guide rod to the retractor. The assembly may be placed on a lateral side of a medial collateral ligament of a knee joint to retract the medial collateral ligament away from a tibial plateau of the knee joint and protect the medial collateral ligament during a tibial plateau resection procedure.

12 Claims, 14 Drawing Sheets

(56) References Cited

U.S. PATENT DOCUMENTS

| | | |
|---|---|---|
| 6,254,532 B1 | 7/2001 | Paolitto |
| 7,077,805 B1 * | 7/2006 | Masson ................ A61B 17/025 600/210 |
| 7,458,933 B2 * | 12/2008 | LeVahn .............. A61B 17/0293 623/20.14 |
| 9,408,598 B1 | 8/2016 | Fantini |
| 2004/0147812 A1 | 7/2004 | Hamel |
| 2013/0131648 A1 | 5/2013 | Haddad |
| 2017/0007225 A1 | 1/2017 | Ferro |
| 2020/0275917 A1 | 9/2020 | Nguyen |

FOREIGN PATENT DOCUMENTS

| | | | |
|---|---|---|---|
| DE | 2808970 A1 | 9/1979 | |
| EP | 1559375 A1 * | 8/2005 | ........... A61B 17/154 |

* cited by examiner

LIGAMENT RETRACTOR

CROSS-REFERENCE TO RELATED APPLICATIONS

The present application claims the benefit of U.S. Provisional Patent Application Ser. No. 62/812,245 entitled "LIGAMENT RETRACTOR" which was filed on Feb. 28, 2019. The above-referenced application is incorporated by reference herein as though set forth in its entirety.

TECHNICAL FIELD

The present disclosure relates to surgical instruments, systems, and methods. More specifically, the present disclosure relates to improved surgical instruments, systems, and methods for retracting ligaments in order to facilitate surgical procedures, such as a knee joint arthroplasty.

BACKGROUND

Joint arthroplasty procedures are surgical procedures in which one or more articulating surfaces of a joint are replaced with prosthetic articulating surfaces. Such procedures are becoming increasingly commonplace, particularly for knee joints. An arthroplasty procedure $c_cb°$ for a knee joint can include implanting a tibial prosthesis to replace the articulating surfaces of the tibia. This may or may not be performed along with replacement of the articulating surfaces of the femur and/or the patella.

For a successful knee joint arthroplasty, it is important to protect certain ligaments of the knee joint from accidental damage during bone resection operations performed during a knee joint arthroplasty procedure. For example, performing a tibial plateau resection operation can carry an increased risk of accidentally damaging or cutting the medial collateral ligament, especially when a surgeon blindly approaches the medial collateral ligament from the lateral side with a saw blade during a tibial plateau resection procedure.

Accordingly, surgical instruments, systems, and methods that can reduce or eliminate the risk of accidentally damaging or cutting ligaments during a surgical procedure would be desirable.

SUMMARY

The various surgical instruments, systems, and methods of the present disclosure have been developed in response to the present state of the art, and in particular, in response to the problems and needs in the art that have not yet been fully solved by currently available surgical instruments, systems, and methods. The surgical instruments, systems, and methods of the present disclosure may provide a reduced risk of accidentally damaging or cutting ligaments during a bone resection operation.

According to some embodiments, an assembly may include a retractor and a guide rod. The retractor may include a retractor handle extending along a first longitudinal axis and a retractor member. The retractor member may include a generally arcuate projection having a proximal end coupled to the retractor handle, a distal end transversely projecting away from the first longitudinal axis, a superior surface, an inferior surface, a convex retractor surface extending intermediate the superior and inferior surfaces, and a concave cutting shield surface located opposite the retractor surface and extending intermediate the superior and inferior surfaces. The guide rod may include an elongate member having a rod proximal end and a rod distal end. The elongate member may extend along a second longitudinal axis. The guide rod may also include a rod coupling feature coupled to the distal end of the elongate member and projecting transversely away from the second longitudinal axis. The rod coupling feature may be configured to pivotably couple the guide rod to the retractor.

In some embodiments, the retractor member may include a guide projection coupled to the cutting shield surface and projecting toward the first longitudinal axis.

In some embodiments, the guide projection may include an attachment aperture formed through the guide projection and a chamfered surface that at least partially surrounds the attachment aperture. The rod coupling feature may be shaped to be received within the attachment aperture formed in the guide projection in order to pivotably couple the guide rod to the retractor.

In some embodiments, the rod coupling feature may include a hook member. The hook member may include a proximal hook surface and a distal hook surface. In some embodiments at least a portion of the proximal hook surface may extend toward the rod proximal end at a first angle and the proximal hook surface may be configured to pivotably couple the guide rod to the retractor. In some embodiments, at least a portion of the distal hook surface may extend toward the rod proximal end at a second angle.

In some embodiments, the distal hook surface may be configured to engage the chamfered surface to facilitate decoupling of the guide rod from the retractor when a distally directed force of sufficient magnitude is applied to the guide rod.

In some embodiments, the proximal hook surface may extend about a proximal end of the hook member from a first side of the hook member to a second side of the hook member.

In some embodiments, the first side of the hook member and the second side of the hook member may be angled together towards a superior side of the hook member.

In some embodiments, the superior side of the hook member comprises a hook member tip projecting toward the rod proximal end above at least a portion of the proximal hook surface.

In some embodiments, at least a portion of the proximal hook surface comprises a cam surface.

In some embodiments, a first portion the proximal hook surface may be concave and a second portion the proximal hook surface may be convex.

In some embodiments, the retractor surface and the cutting shield surface may each decrease in height moving from the proximal end of the arcuate projection to the distal end of the arcuate projection.

In some embodiments, the retractor may further include at least one of: a pointed tip located at the distal end of the arcuate projection; a lower concave curvature formed in the inferior surface of the arcuate projection and located proximal the pointed tip; a lower convex curvature formed in the inferior surface of the arcuate projection and located proximal the lower concave curvature; and a notch located intermediate the retractor handle and the retractor member.

In other embodiments, a method for retracting a medial collateral ligament of a knee joint with an assembly may include pivotally coupling a guide rod to a retractor by engaging a rod coupling feature of the guide rod with a retractor coupling feature of the retractor. The method may also include inserting the assembly into an incision at a surgical site proximal a knee joint and maneuvering the assembly relative to the knee joint to place the assembly on a lateral side of a medial collateral ligament of the knee joint.

In some embodiments, the method may also include decoupling the guide rod from the retractor by applying a distally directed force to the guide rod and removing the guide rod from the knee joint.

In some embodiments, the method may also include retracting the medial collateral ligament away from a tibial plateau of the knee joint with the retractor.

In some embodiments, the method may also include resecting at least a portion of the tibial plateau with a bone saw while retracting the medial collateral ligament away from the tibial plateau to prevent damaging the medial collateral ligament with the bone saw.

In yet other embodiments, a method for retracting a medial collateral ligament of a knee joint with a retractor having a generally arcuate projection having a convex retractor surface and a concave cutting shield surface may include inserting the retractor into an incision at a surgical site proximal the knee joint and maneuvering the retractor relative to the knee joint to ° locate the retractor on a lateral side of the medial collateral ligament.

In some embodiments, the method may also include retracting the medial collateral ligament away from a tibial plateau of the knee joint with the convex retractor surface.

In some embodiments, the method may also include resecting at least a portion of the tibial plateau with a bone saw while retracting the medial collateral ligament away from the tibial plateau in order to prevent damaging the medial collateral ligament with the bone saw.

In some embodiments, the method may also include resecting at least a portion of a tibial plateau of the knee joint with a bone saw while the concave cutting shield surface prevents the bone saw from damaging the medial collateral ligament.

These and other features and advantages of the present disclosure will become more fully apparent from the following description and appended claims, or may be learned by the practice of the instruments, systems, and methods set forth hereinafter.

BRIEF DESCRIPTION OF THE DRAWINGS

Exemplary embodiments of the disclosure will become more fully apparent from the following description and appended claims, taken in conjunction with the accompanying drawings. Understanding that these drawings depict only exemplary embodiments and are, therefore, not to be considered limiting of the scope of the appended claims, the exemplary embodiments of the present disclosure will be described with additional specificity and detail through use of the accompanying drawings in which:

Figure 1A:
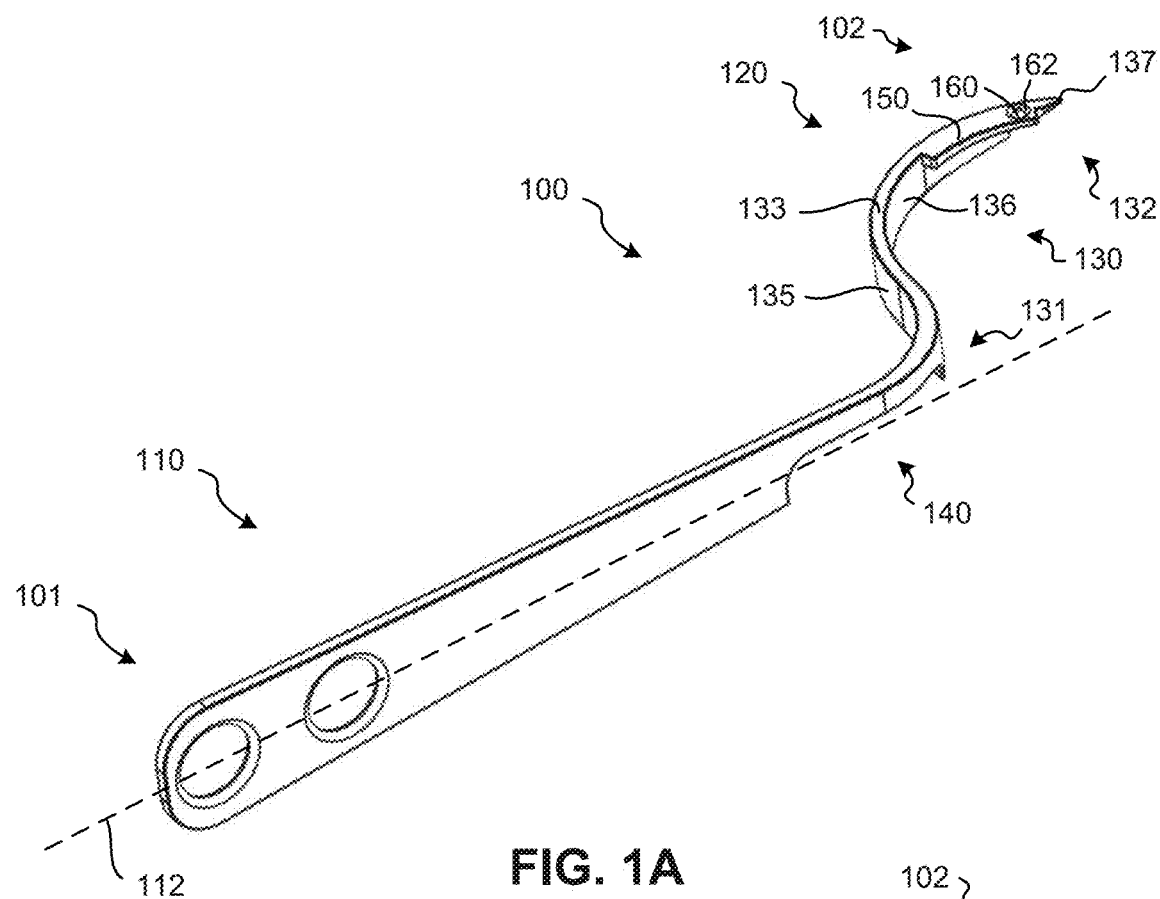
FIG. 1A is a perspective view of a retractor, according to an embodiment of the present disclosure.
Figure 1B:
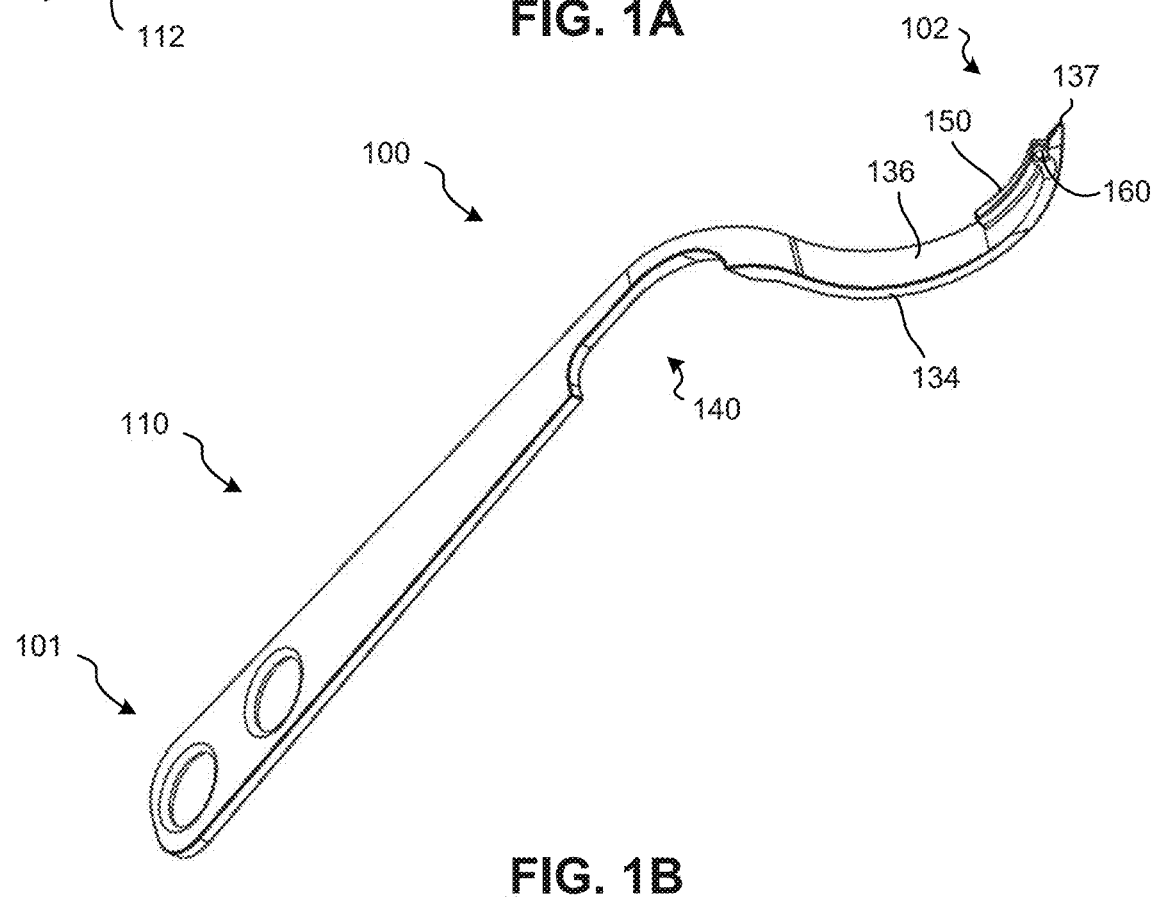
FIG. 1B is another perspective view of the retractor of FIG. 1A.
Figure 1C:
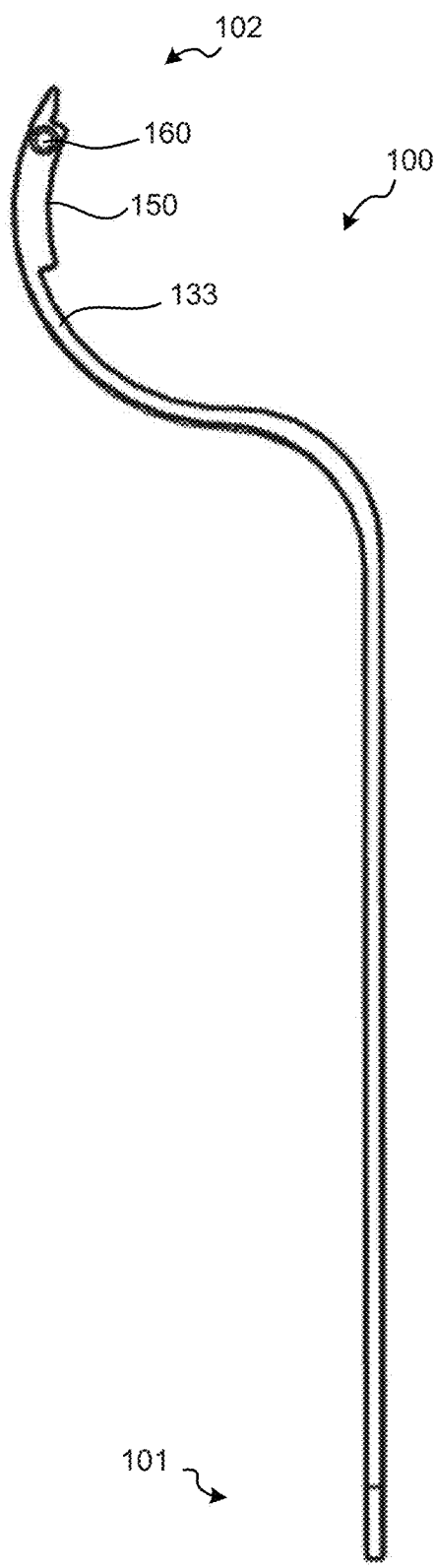
FIG. 1C is a top view of the retractor of FIG. 1A.
Figure 1D:
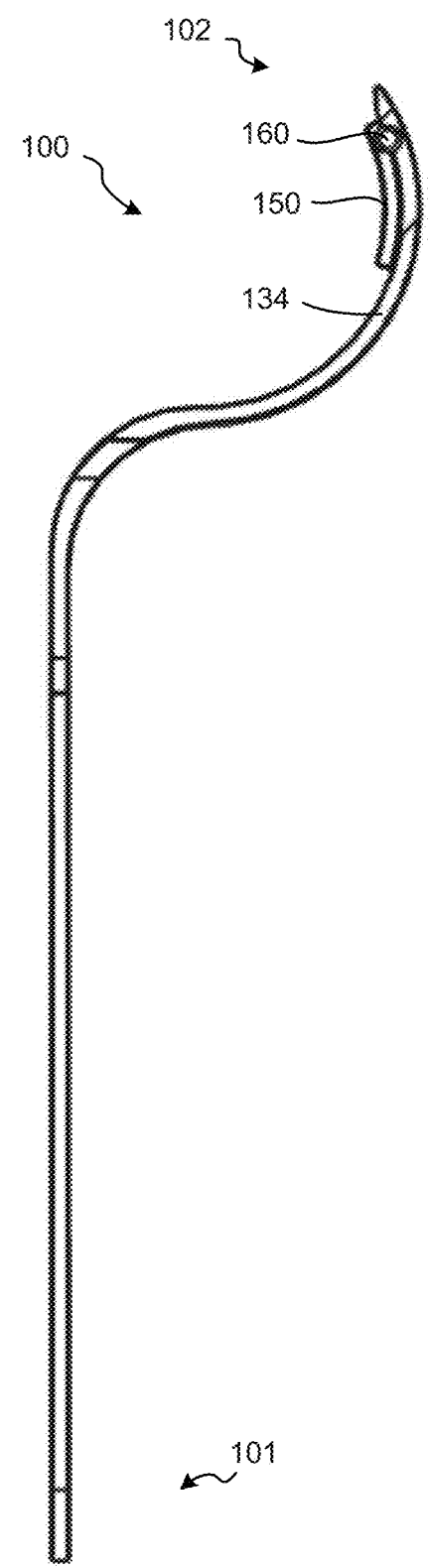
FIG. 1D is a bottom view of the retractor of FIG. 1A.

It is to be understood that the drawings are for purposes of illustrating the concepts of the disclosure and may not be drawn to scale. Furthermore, the drawings illustrate exemplary embodiments and do not represent limitations to the scope of the present disclosure.

DETAILED DESCRIPTION

Exemplary embodiments of the present disclosure will be best understood by reference to the drawings, wherein like parts are designated by like numerals throughout. It will be readily understood that the components of the present disclosure, as generally described and illustrated in the Figures herein, could be arranged and designed in a wide variety of different configurations. Thus, the following more detailed description of the embodiments of the apparatus, systems, and method, as represented in the Figures, is not intended to limit the scope of the present disclosure, as claimed in this or any other application claiming priority to this application, but is merely representative of exemplary embodiments of the present disclosure.

Standard medical directions, planes of reference, and descriptive terminology are employed in this specification. For example, anterior means toward the front of the body. Posterior means toward the back of the body. Superior, or caudal, means toward the head. Inferior, or cephalad, means toward the feet. Medial means toward the midline of the body. Lateral means away from the midline of the body.

Axial means toward a central axis of the body. Abaxial means away from a central axis of the body. Ipsilateral means on the same side of the body. Contralateral means on the opposite side of the body. A sagittal plane divides a body into right and left portions. A midsagittal plane divides the body into bilaterally symmetric right and left halves. A coronal plane divides a body into anterior and posterior portions. A transverse plane divides a body into superior and inferior portions. These descriptive terms may be applied to an animate or inanimate body.

FIGS. 1A-1I illustrate various views of a retractor 100, according to an embodiment of the present disclosure. The retractor 100 may generally include a proximal end 101, a distal end 102, a retractor handle 110 at the proximal end 101, and a retractor member 120 at the distal end 102 which may be coupled to the retractor handle 110. The retractor handle 110 may generally extend along a first longitudinal axis 112, as shown in FIG. 1. However, it will be understood that the retractor handle 110 or portions of the retractor handle 110 may or may not extend along the first longitudinal axis 112 in a straight line. For example, the phrase "extending along an axis" may apply to any straight and/or curved member that extends parallel to the axis, or follows a path that maintains a proximity to the axis.

The retractor member 120 may include a generally arcuate projection, or arcuate projection 130, and a retractor coupling feature (e.g., such as a guide projection 150 having an attachment aperture 160, as one non-limiting example, which will be discussed in more detail below).

As defined herein, the terms "generally arcuate" and/or "arcuate" mean having a curved shape, an arc shape, a "bow-like" shape, etc. The terms "generally arcuate" and/or "arcuate" include any curved shape that follows a generally arcuate pathway, and do not require that the shape maintain a precisely constant radius of curvature. An "arcuate" or "generally arcuate" shape may be defined by a curvilinear surface, or by a series of rectilinear segments that defines a curved pathway.

The arcuate projection 130 may transversely project away from the first longitudinal axis 112. The arcuate projection 130 may include a proximal end 131 (which may be coupled to the retractor handle 110 and/or coupled to a notch 140 formed intermediate the retractor handle 110 and the retractor member 120), a distal end 132, a superior surface 133, and an inferior surface 134. The arcuate projection 130 may also include a retractor surface 135 that extends intermediate the superior surface 133 and the inferior surface 134. The retractor surface 135 may have a convex curvature. The arcuate projection 130 may further include a cutting shield surface 136, opposite the retractor surface 135, which may extend intermediate the superior surface 133 and the inferior surface 134. The cutting shield surface 136 may have a concave curvature.

Figure 1E:
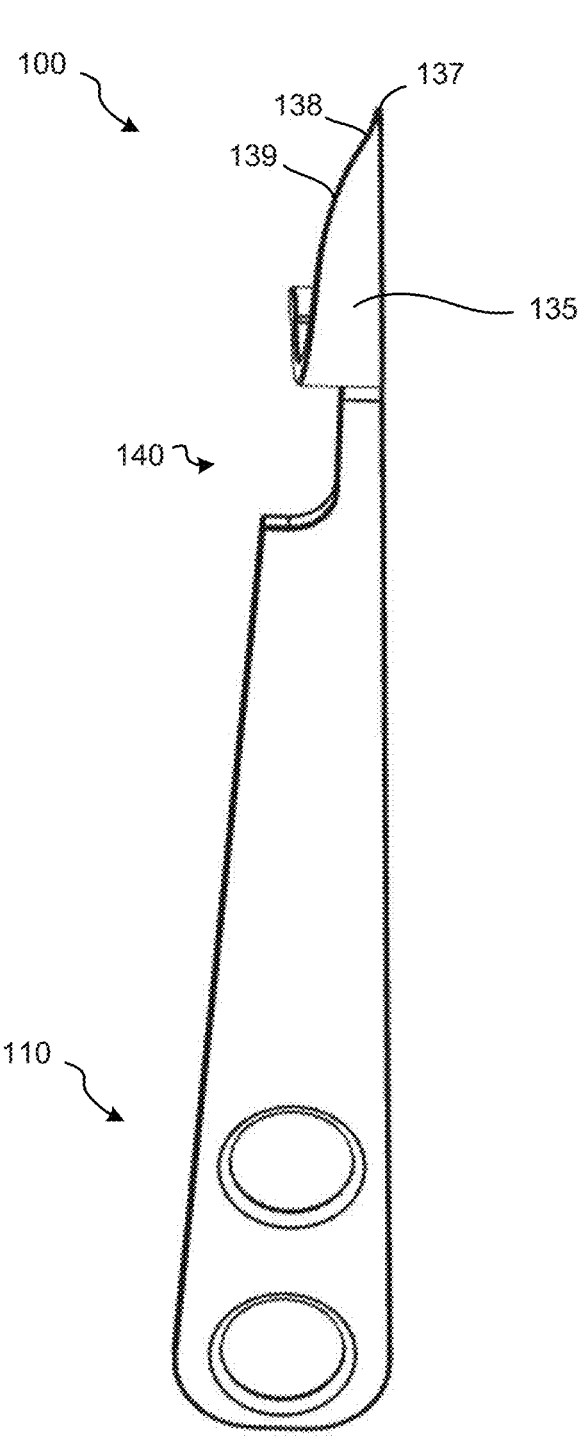
FIG. 1E is a left side view of the retractor of FIG. 1A.
Figure 1F:
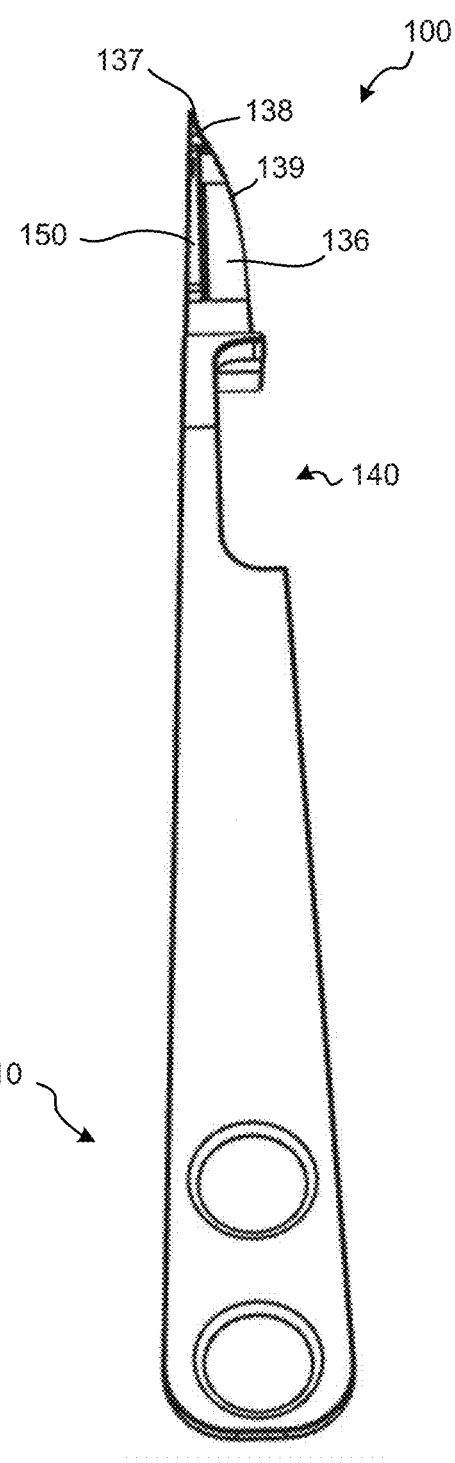
FIG. 1F is a right side view of the retractor of FIG. 1A.
Figure 1G:
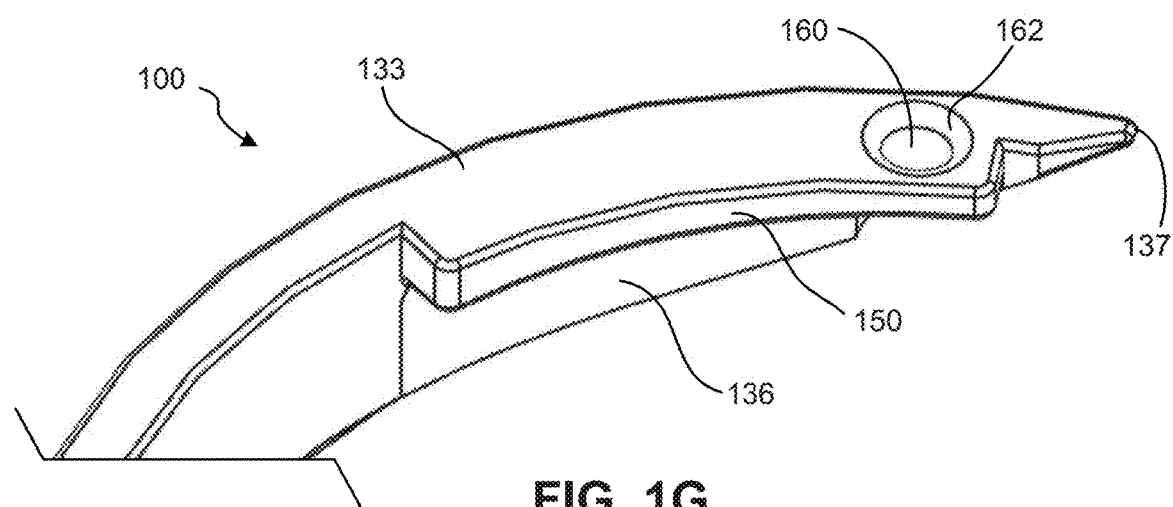
FIG. 1G is a perspective top view of the distal end of the retractor of FIG. 1A.
Figure 1H:
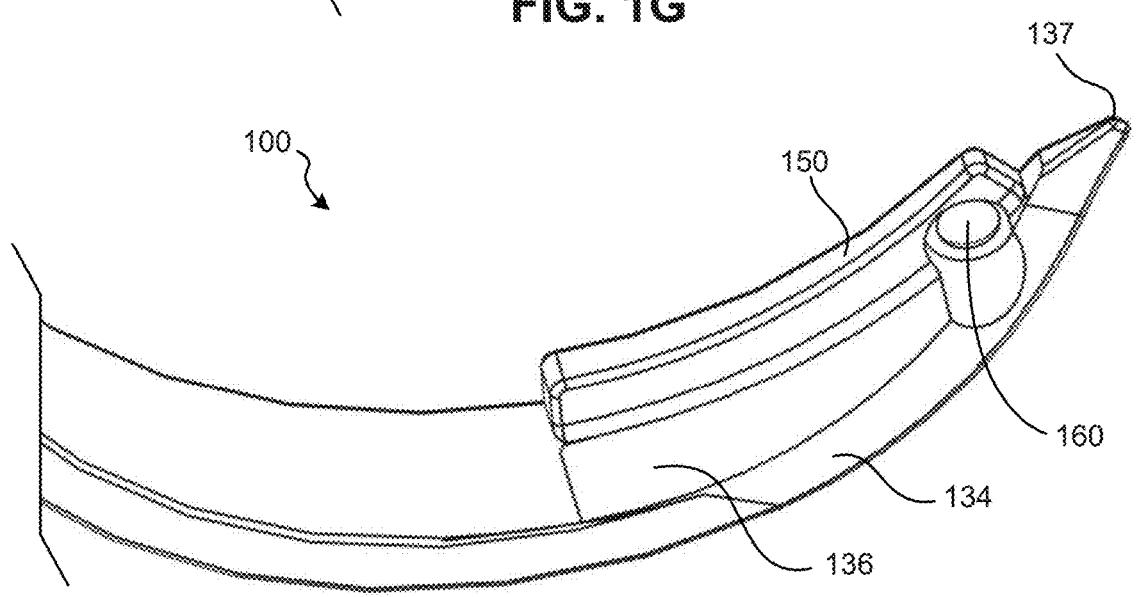
FIG. 1H is a perspective bottom view of the distal end of the retractor of FIG. 1A.
Figure 1I:
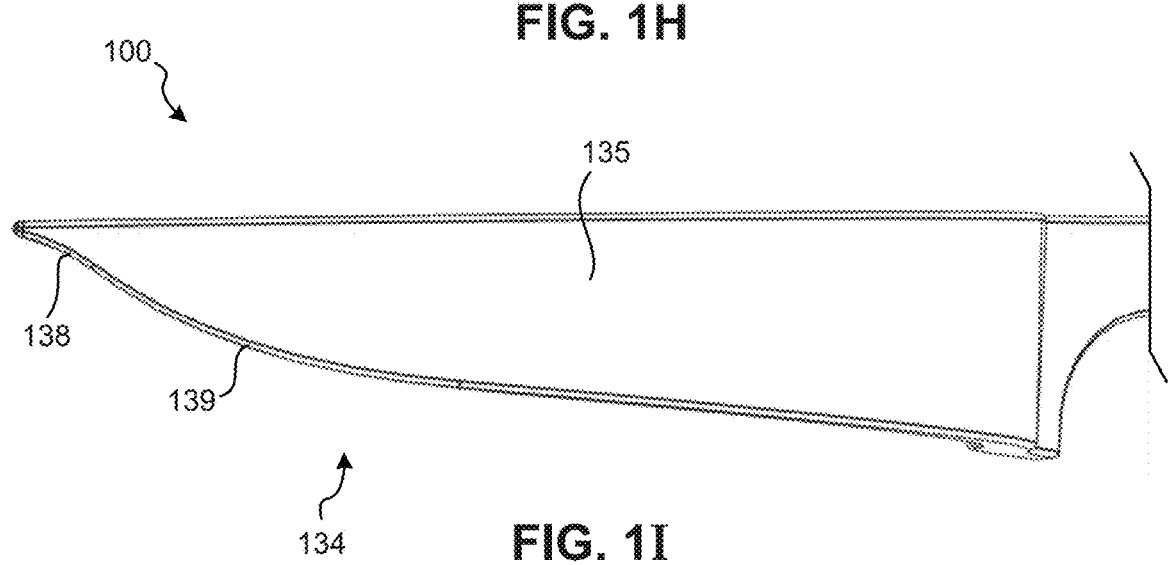
FIG. 1I is a left side view of the distal end of the retractor of FIG. 1A.

The distal end 132 of the arcuate projection 130 may include a pointed tip 137. The distal end 132 of the arcuate projection 130 near the pointed tip 137 may also include a lower concave curvature 138 and a lower convex curvature 139 that may be formed in the inferior surface 134 of the arcuate projection 130, as shown in FIGS. 1E, 1F, and 1I. Each of the pointed tip 137, the concave curvature 138, and/or the convex curvature 139, may help facilitate maneuvering of the distal end 102 of the retractor 100 within a tight knee joint during a surgical procedure. Moreover, the retractor surface 135 and the cutting shield surface 136 of the arcuate projection 130 may both generally decrease in height moving from the proximal end 131 of the arcuate projection 130 toward the distal end 132 of the arcuate projection 130 to further aid maneuvering of the distal end 102 of the retractor 100 within a tight knee joint, as can be seen in FIG. 1I.

In some embodiments, the retractor coupling feature may comprise a guide projection 150. The guide projection 150 may be coupled to the cutting shield surface 136 of the arcuate projection 130 and may project toward the first longitudinal axis 112. The guide projection 150 may be configured to rest on top of a tibial plateau during a knee joint arthroplasty procedure in order to help properly place the retractor 100 during a tibial plateau resection, as will be discussed in more detail below. The guide projection 150 may also include an attachment aperture 160 formed in, or through, the guide projection 150. The attachment aperture 160 may also include a chamfered surface 162, as will be discussed in more detail below.

Figure 2A:
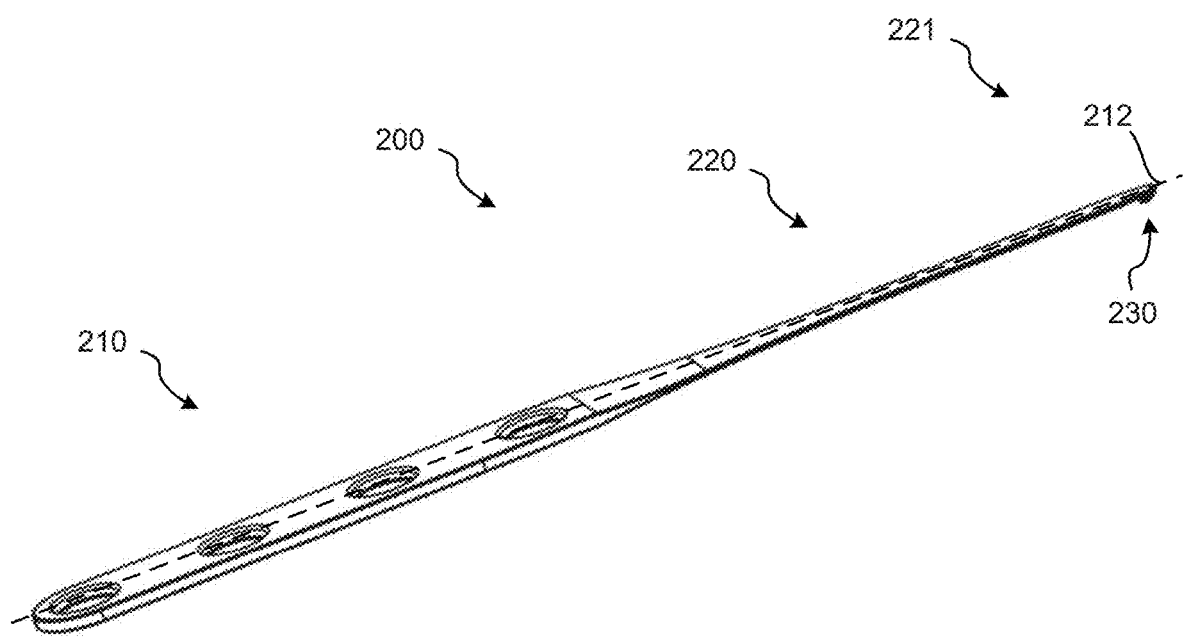
FIG. 2A is a perspective view of a guide rod, according to an embodiment of the present disclosure.
Figure 2B:
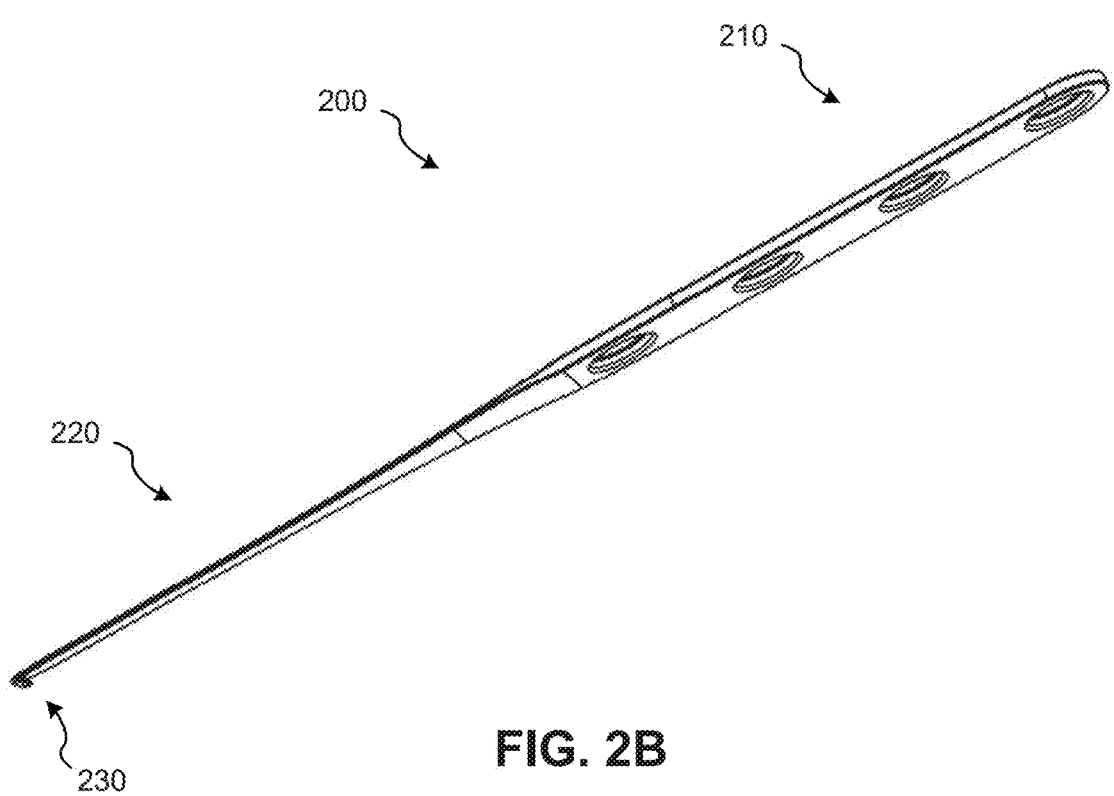
FIG. 2B is another perspective view of the guide rod of FIG. 2A.
Figure 2C:
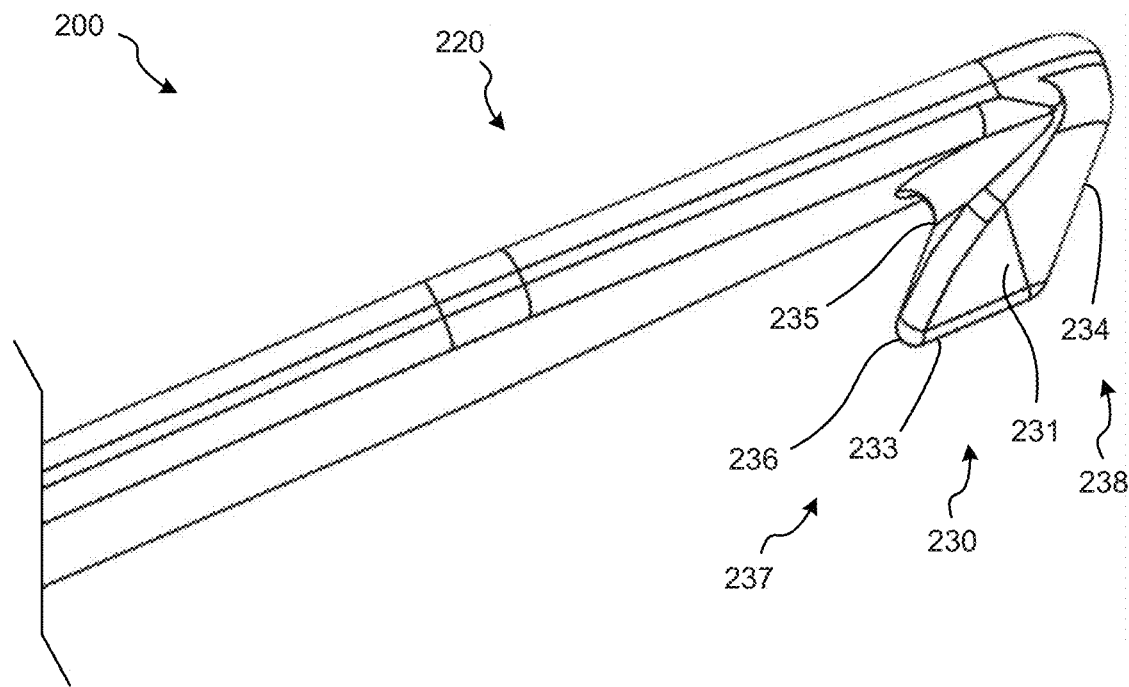
FIG. 2C is a perspective bottom view of the distal end of the guide rod of FIG. 2A.
Figure 2D:
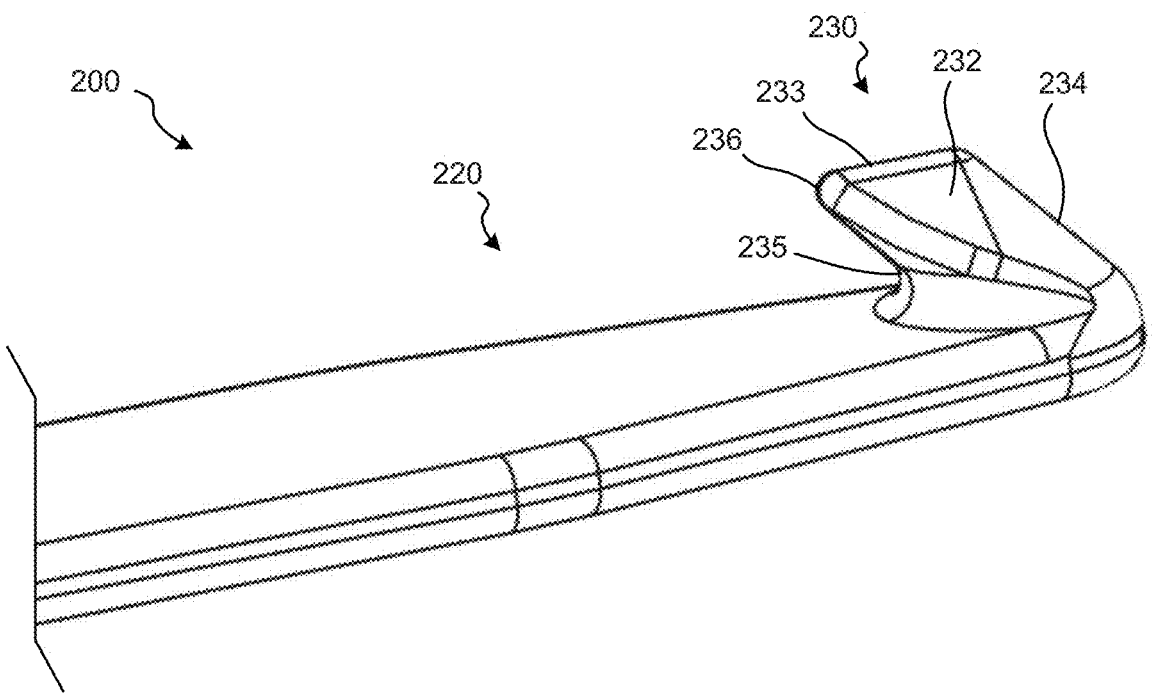
FIG. 2D is another perspective bottom view of the distal end of the guide rod of FIG. 2A.
Figure 2E:
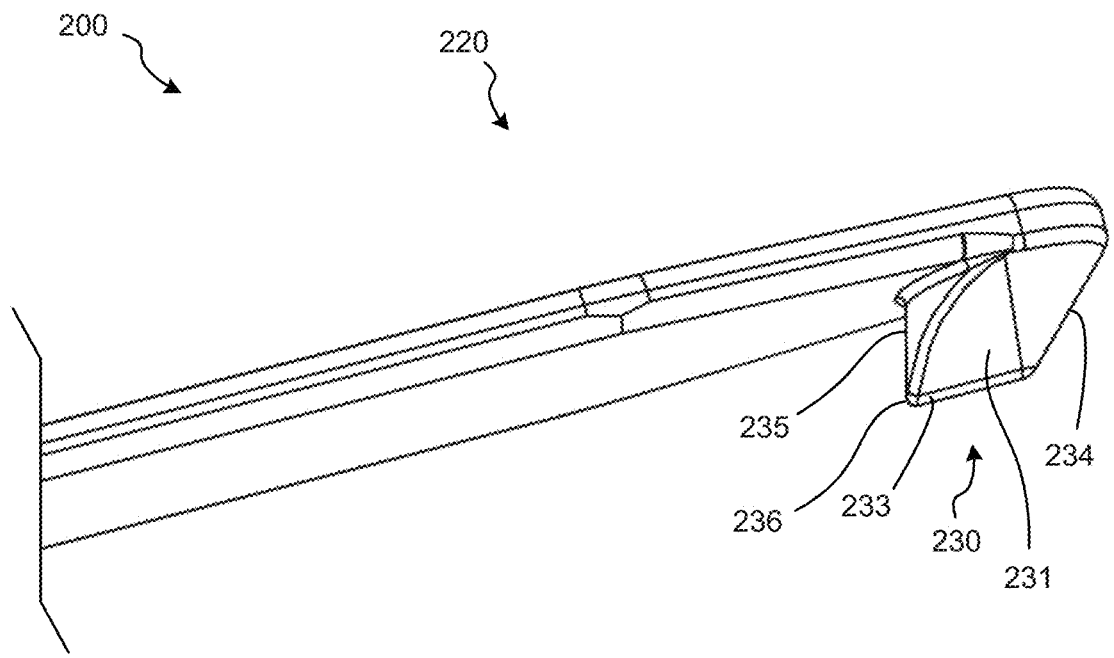
FIG. 2E is a perspective bottom view of the distal end of the guide rod of FIG. 2A with an alternative hook member shape.
Figure 2F:
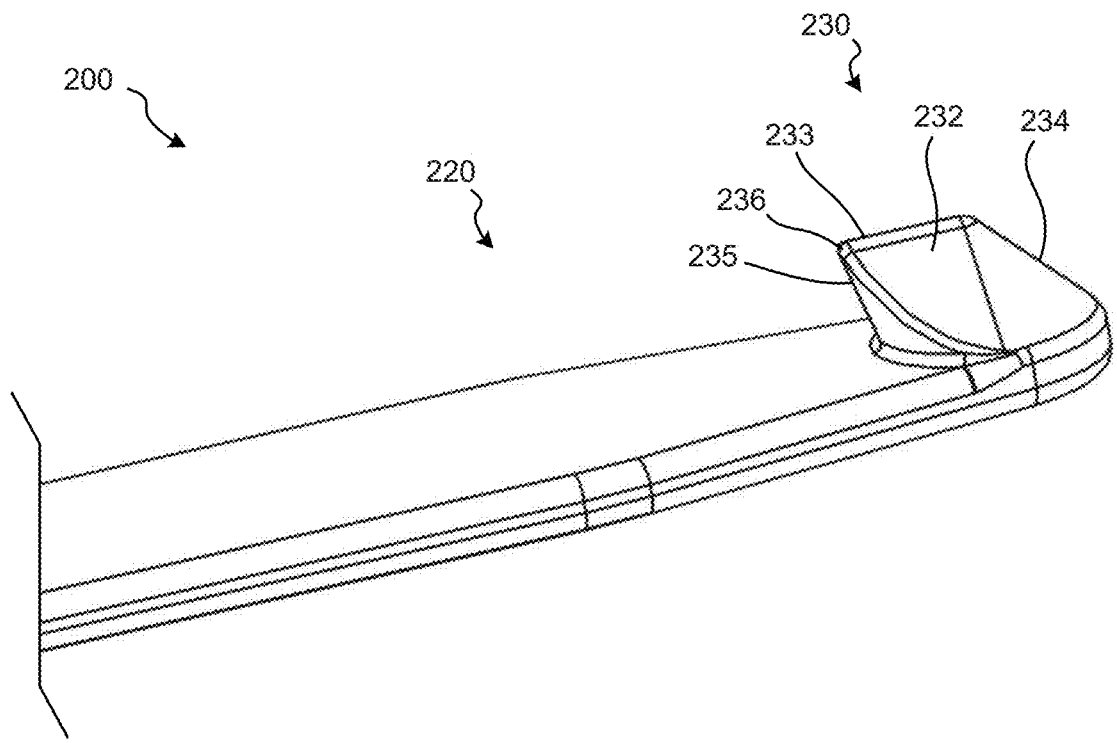
FIG. 2F is another perspective bottom view of the distal end of the guide rod of FIG. 2E.
Figure 2G:
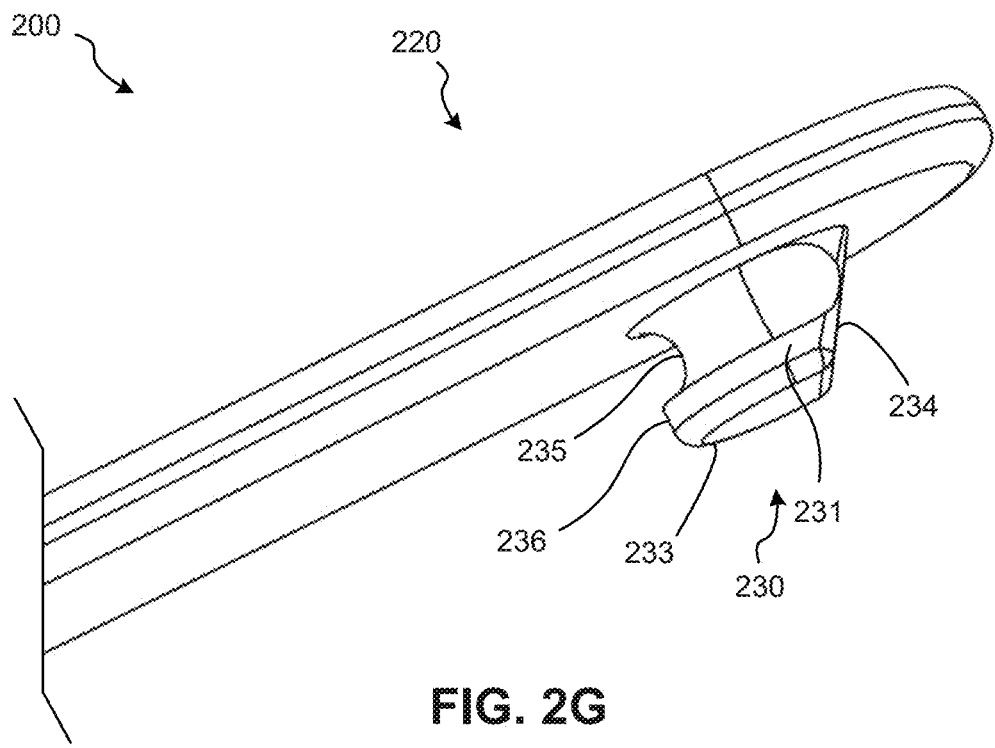
FIG. 2G is a perspective bottom view of the distal end of the guide rod of FIG. 2A with an alternative shape and hook member design.
Figure 2H:
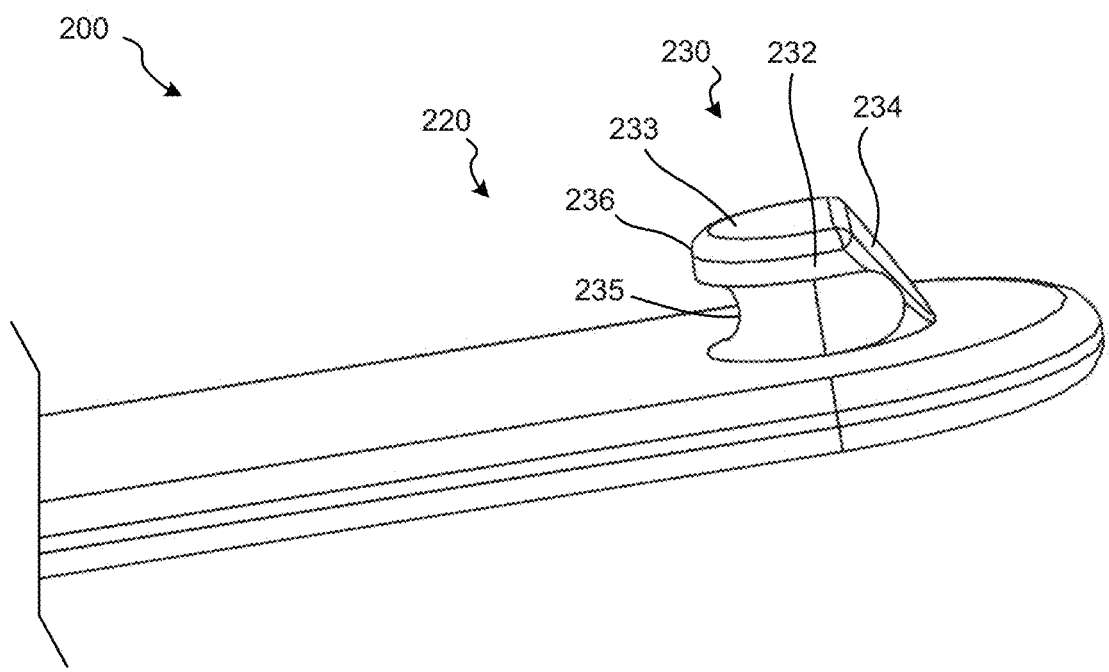
FIG. 2H is another perspective bottom view of the distal end of the guide rod of FIG. 2H.

FIGS. 2A-2H illustrate various views of a guide rod 200, according to embodiments of the present disclosure. The guide rod 200 may generally include a guide rod handle 210 and an elongate member 220 that may be coupled to the guide rod handle 210 and/or integrally formed therewith. The elongate member 220 may include a proximal end, or rod proximal end 222, and a rod coupling feature (e.g., such as a hook member 230, as one non-limiting example, which will be discussed below in more detail) that may be coupled to a distal end, or rod distal end 221, of the elongate member 220. The guide rod handle 210 and/or the elongate member 220 may generally extend a long a second longitudinal axis 212, as shown in FIG. 2A.

In some embodiments, the rod coupling feature of the guide rod 200 may be configured to engage the retractor coupling feature of the retractor 100 in order to pivotably couple the guide rod 200 to the retractor 100 and form an assembly 10, as will be discussed below in more detail with respect to FIGS. 3-6.

Although specific example structures for the retractor coupling feature and the rod coupling feature are presented herein, it will be understood that these are mere exemplary structures given for illustration purposes only. Accordingly, any suitable shape, form, structure, feature, etc., is contemplated herein that can form a retractor coupling feature and/or a corresponding rod coupling feature that may engage with each other to pivotably couple the guide rod 200 to the retractor 100, without departing from the spirit or scope of the present disclosure.

In some embodiments, the rod coupling feature may comprise a hook member 230. The hook member 230 may transversely project away from the elongate member 220 and/or the second longitudinal axis 212. The hook member 230 may be shaped to be received within the attachment aperture 160 formed in the guide projection 150 of the retractor 100 in order to pivotably couple the guide rod 200 to the retractor 100. The hook member 230 may assume any suitable shape in order to pivotably couple the guide rod 200 to the retractor 100. FIGS. 2C-2H illustrate three non-limiting examples of hook members 230 having different shapes that may be configured to pivotably couple the guide rod 200 to the retractor 100. However, it will also be understood that any number of differently shaped hook members that can pivotably couple the guide rod 200 to the retractor 100 are envisioned herein. The hook member 230 may generally include a first side 231, a second side 232, a superior side 233, a distal hook surface 234 located at a distal end 238 of the hook member 230, a proximal hook surface 235 located at a proximal end 237 of the hook member 230, and a hook member tip 236.

In some embodiments, the proximal hook surface 235 may extend about a proximal end 237 of the hook member 230 from the first side 231 to the second side 232.

In some embodiments, at least a portion of the proximal hook surface 235 may extend toward the guide rod handle 210, or rod proximal end 222, at a first angle. The shape and/or angle of the proximal hook surface 235 may be selected to facilitate pivotable coupling of the guide rod 200 to the retractor 100.

In some embodiments, the hook member tip 236 may extend or project toward the rod proximal end 222 above at least a portion of the proximal hook surface 235.

In some embodiments, at least a portion of the proximal hook surface 235 may comprise a cam surface configured to interact with a surface associated with the attachment aperture 160.

In some embodiments, at least a portion of the proximal hook surface 235 may be concave.

In some embodiments, at least a portion of the proximal hook surface 235 may be convex.

In some embodiments, at least a portion of the distal hook surface 234 may generally extend toward the guide rod handle 210, or rod proximal end 222, at a second angle.

In some embodiments, the shape and/or second angle of the distal hook surface 234 may be selected to engage the chamfered surface 162 of the attachment aperture 160 in order to facilitate decoupling of the guide rod 200 from the retractor 100 when a distally directed force of sufficient magnitude is applied to the guide rod 200 relative to the retractor 100.

In some embodiments, the first side 231 and the second side 232 may angle together towards the superior side 233 of the hook member 230.

Figure 3:
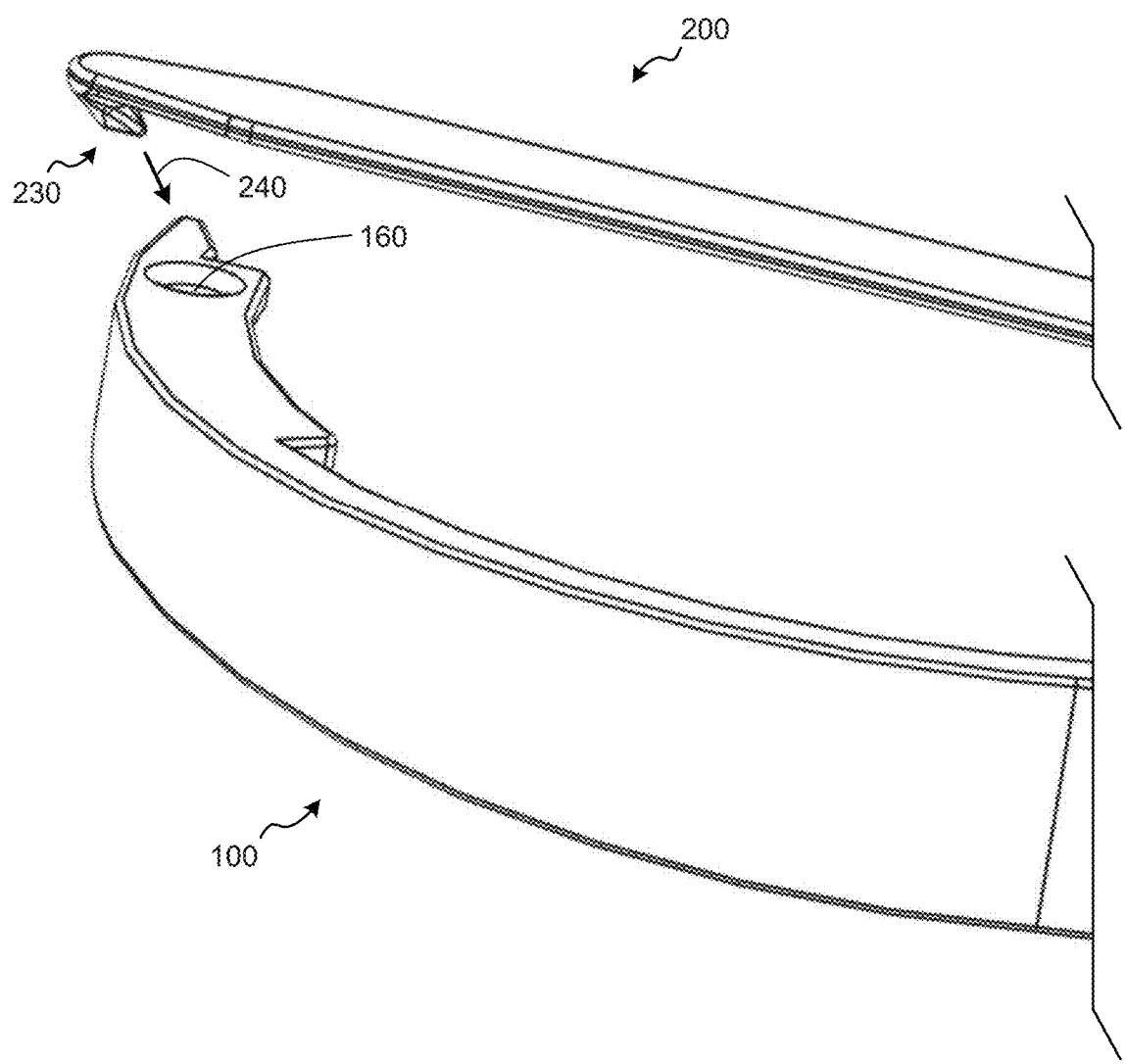
FIG. 3 is a perspective view of the distal end of the retractor of FIG. 1A and the distal end of the guide rod of FIG. 2A, prior to assembly.

FIG. 3 is a perspective view of the distal ends of the retractor 100 and guide rod 200 before they are assembled together. A surgeon may assemble the retractor 100 and the guide rod 200 together by inserting the hook member 230 into the attachment aperture 160 in the direction of arrow 240 shown in FIG. 3.

Figure 4:
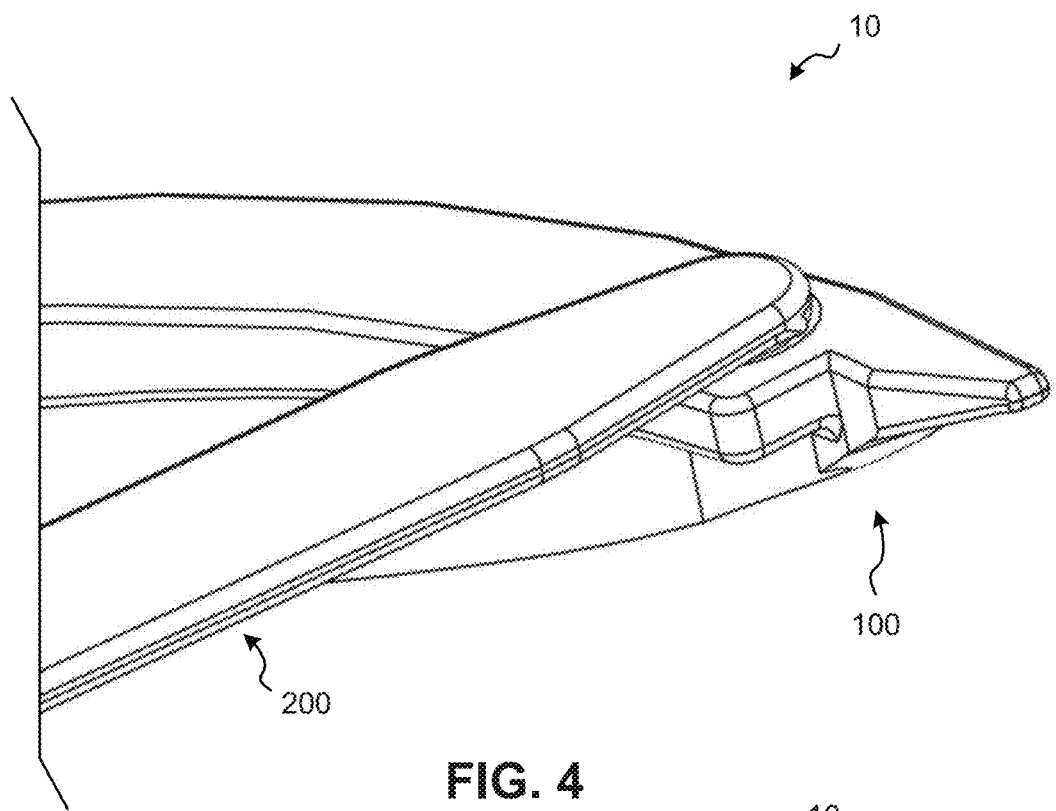
FIG. 4 is a perspective top view of the distal ends of the retractor and guide rod shown in of FIG. 3, after assembly.
Figure 5:
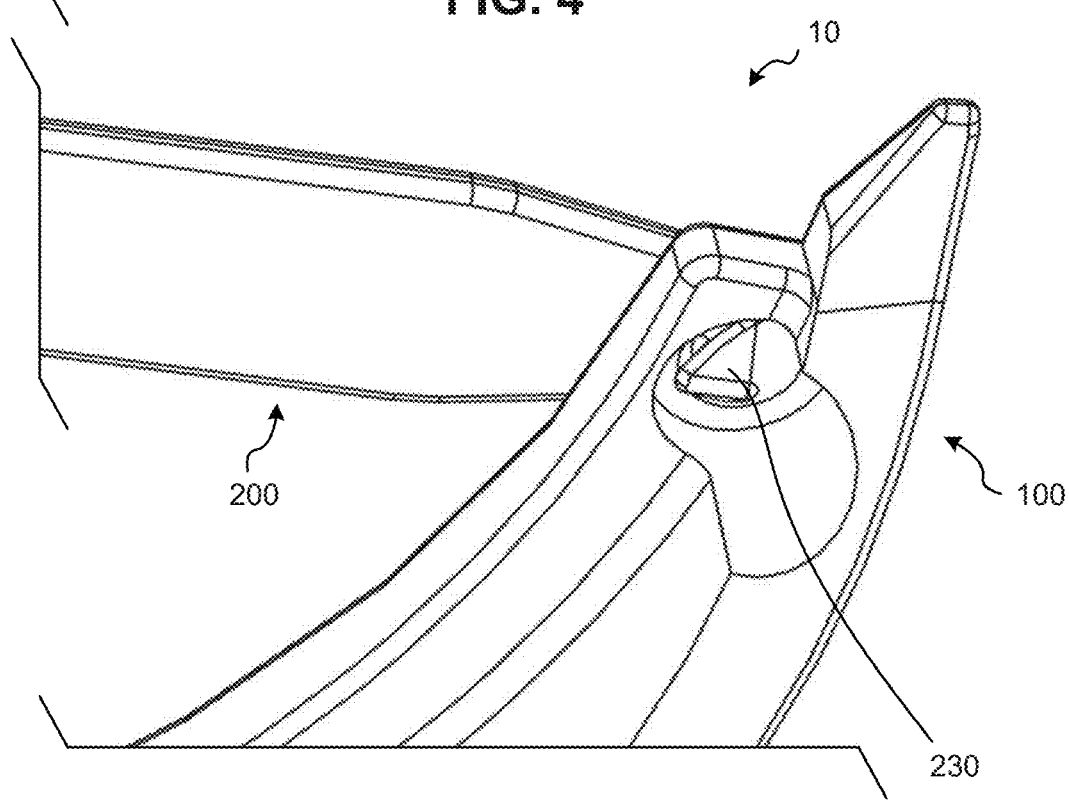
FIG. 5 is a perspective bottom view of the distal ends of the retractor and guide rod shown in of FIG. 3, after assembly.
Figure 6:
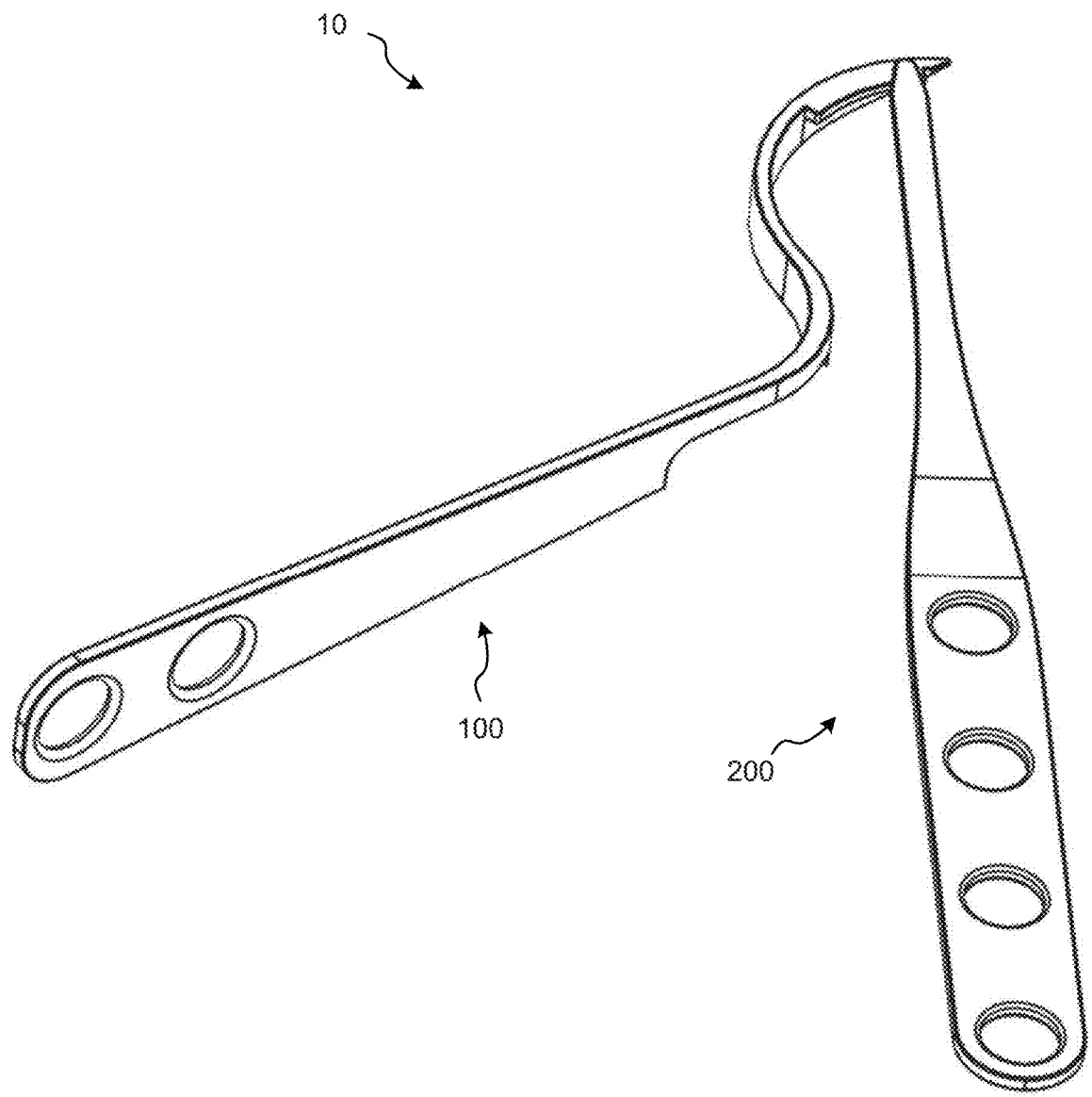
FIG. 6 is a perspective view of the entire assembly of FIGS. 4 and 5.

FIGS. 4-6 illustrate various perspective views of the retractor 100 and guide rod 200 after they have been assembled together to form an assembly 10. As previously discussed, the guide rod 200 may be decoupled from the retractor 100 by applying a distally directed force of sufficient magnitude to the guide rod 200. This will cause the distal hook surface 234 (which may be angled as discussed above) to engage the chamfered surface 162 that surrounds the attachment aperture 160 (which may also be angled in a complementary fashion to the distal hook surface 234) in order to decouple the guide rod 200 from the retractor 100.

Figure 7:
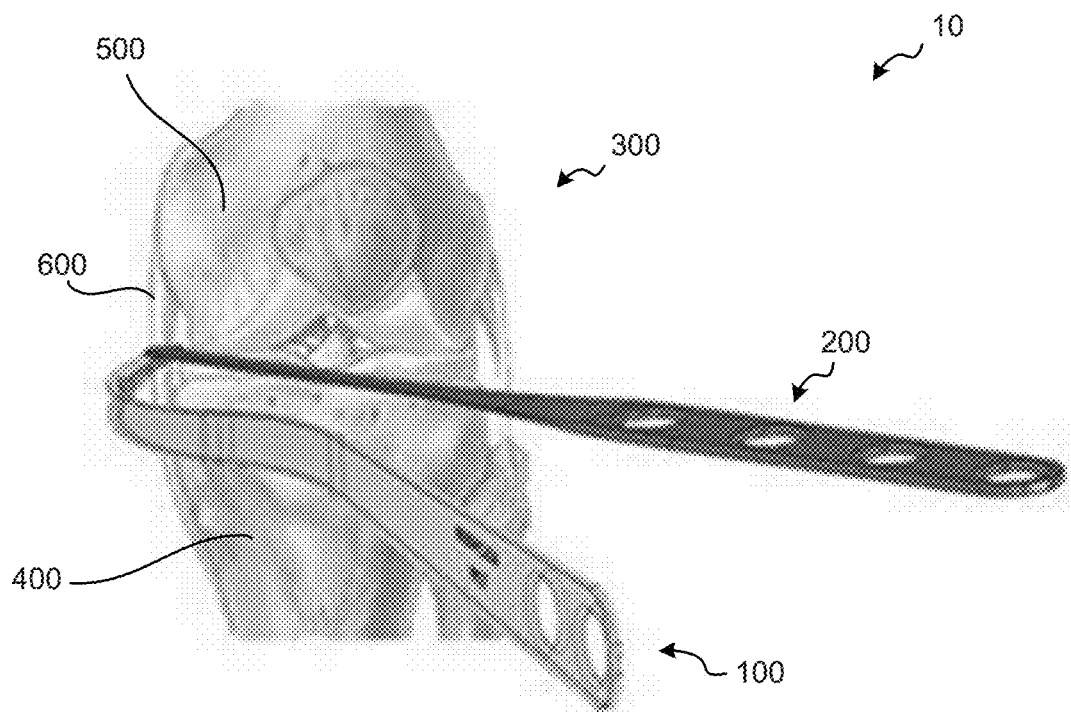
FIG. 7 is a perspective view of the assembly of FIG. 6 inserted into a knee joint during a surgical procedure.

FIG. 7 is a perspective view of the assembly 10 inserted into a knee joint 300 during a surgical procedure. The knee joint 300 may include a tibia 400, a femur 500, and a medial collateral ligament 600. The guide rod 200, pivotably coupled to the retractor 100, helps prevent the distal end of the retractor 100 from being accidentally placed on the medial side of the medial collateral ligament 600 during insertion of the by the surgeon. Rather, the guide rod 200 will help ensure that the distal end of the retractor 100 will be placed on the lateral side of the medial collateral ligament 600 by the surgeon during insertion. Once the distal end of the retractor 100 has been properly positioned on the lateral side of the medial collateral ligament 600, the guide rod 200 may be decoupled from the retractor 100 (as previously discussed) and removed from the knee joint 300.

Figure 8:
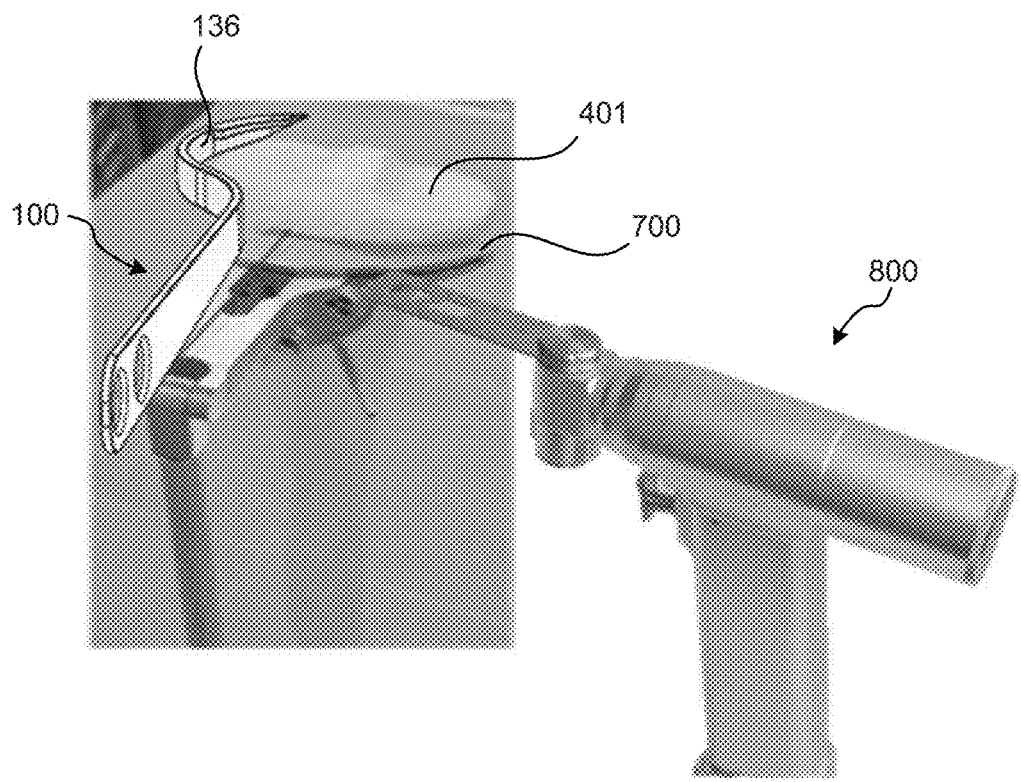
FIG. 8 is a perspective view of the retractor of FIG. 1A relative to a tibia, cutting guide, and bone saw during a tibial plateau resection procedure.

FIG. 8 is a perspective view of the retractor 100, a tibia 401, a cutting guide 700 engaged with the tibia 401, and a bone saw 800, in preparation for a tibial plateau resection procedure. The retractor 100 may be utilized by a surgeon to retract a medial collateral ligament of the knee joint (not shown in FIG. 8) away from the tibial plateau during the resection procedure. The cutting shield surface 136 of the retractor 100 may also act as a mechanical stop to the blade of the bone saw 800 to further protect the medial collateral ligament from accidental damage or cutting during the tibial plateau resection procedure.

Figure 9:
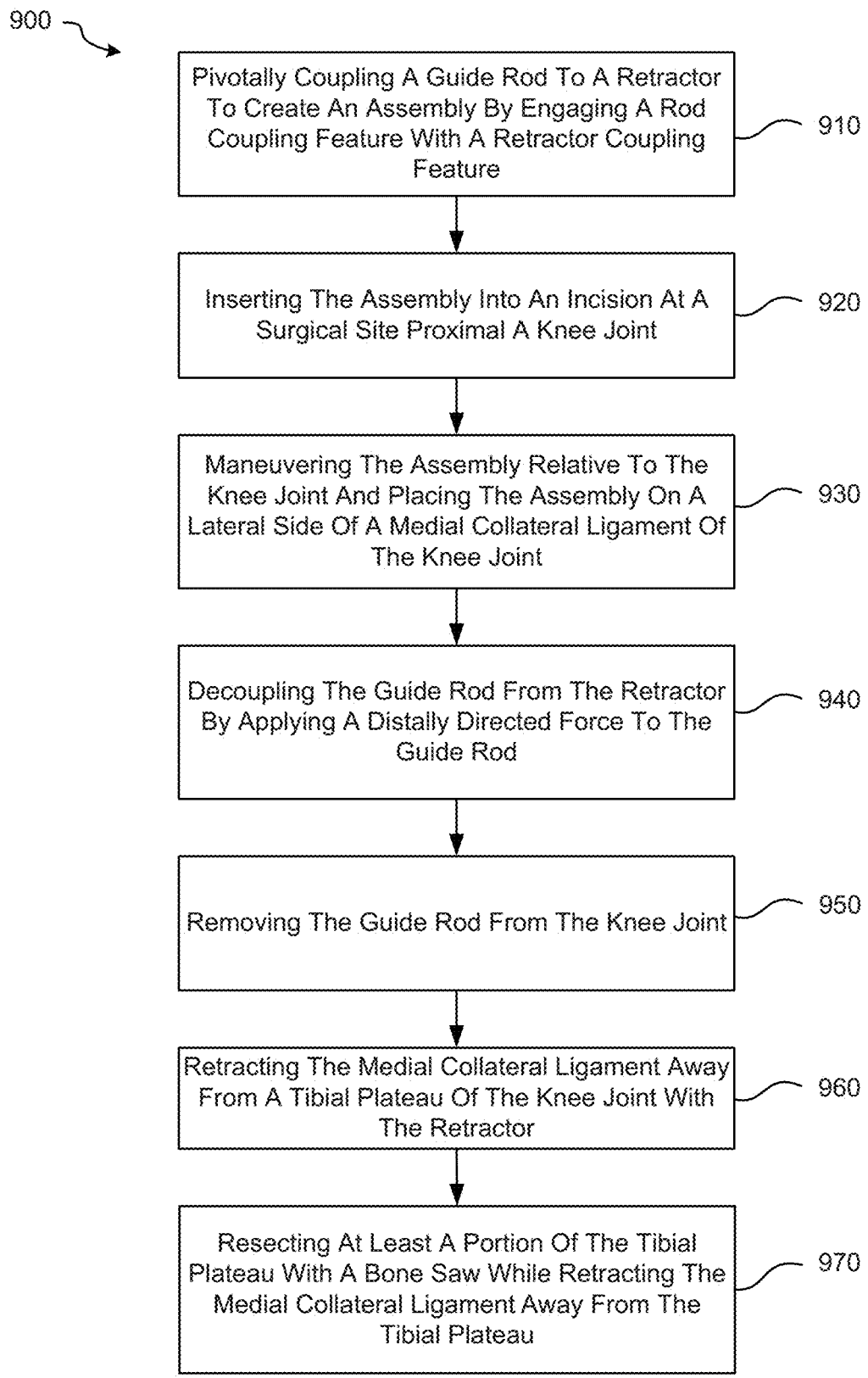
FIG. 9 is a flowchart of a method for retracting a medial collateral ligament with an assembly during a knee joint arthroplasty procedure.

FIG. 9 is a flowchart of a method 900 for retracting a medial collateral ligament with an assembly 10 during a knee joint arthroplasty procedure. The assembly 10 may include a retractor 100 having a retractor coupling feature and a guide rod 200 having a rod coupling feature configured to engage the retractor coupling feature to pivotably couple the guide rod 200 to the retractor 100.

The method 900 may begin with a step 910 in which the guide rod 200 may be pivotally coupled to the retractor 100 to create the assembly 10 by engaging the rod coupling feature with the retractor coupling feature. In some embodiments, this may be accomplished by inserting a hook member 230 of the guide rod 200 into an attachment aperture 160 formed in the distal end of the retractor 100.

Once the guide rod 200 has been coupled to the retractor 100, the method 900 may proceed to a step 920 in which the assembly 10 may be inserted into an incision (not shown) at a surgical site proximal a knee joint.

Once the assembly 10 has been inserted into the incision, the method 900 may proceed to a step 930 in which the assembly 10 may be maneuvered relative to the knee joint in order to place the assembly 10 on a lateral side of a medical collateral ligament of the knee joint. The guide rod 200, coupled to the retractor 100, can ensure the retractor 100 does not end up on the medial side of the medical collateral ligament, as previously discussed.

Alternatively, or in addition thereto, once the assembly 10 has been placed on the lateral side of the medical collateral ligament, the method 900 may proceed to a step 940 in which the guide rod 200 may be decoupled from the retractor 100 by applying a distal force to the guide rod 200 relative to the retractor 100, as previously discussed. The decoupled guide rod 200 may then be removed from the knee joint in a step 950.

Once the guide rod 200 has been decoupled from the retractor 100 and removed from the knee joint, the method 900 may proceed to a step 960 in which the surgeon may utilize the retractor 100 to retract the medial collateral ligament away from a tibial plateau of the knee joint.

Alternatively, or in addition thereto, the method 900 may proceed to a step 970 in which a portion of the tibial plateau may be resected with a bone saw while the medial collateral ligament is retracted away from the tibia, and the method 900 may end.

In this manner, the medial collateral ligament may be protected from damage by the bone saw during the resection procedure. The retractor 100 may protect the medial collateral ligament in at least two ways including: (1) via retraction, which increases a separation distance between the bone saw blade and the medial collateral ligament, thus decreasing the likelihood of damaging the medial collateral ligament; and (2) the cutting shield surface 136 of the retractor 100 may directly shield the medial collateral ligament from the bone saw blade to prevent the bone saw blade from damaging the medial collateral ligament. Thus, the cutting shield surface 136 can help in all instances where the separation distance achieved from retraction may or may not be sufficient to keep the medial collateral ligament away from the bone saw blade.

Figure 10:
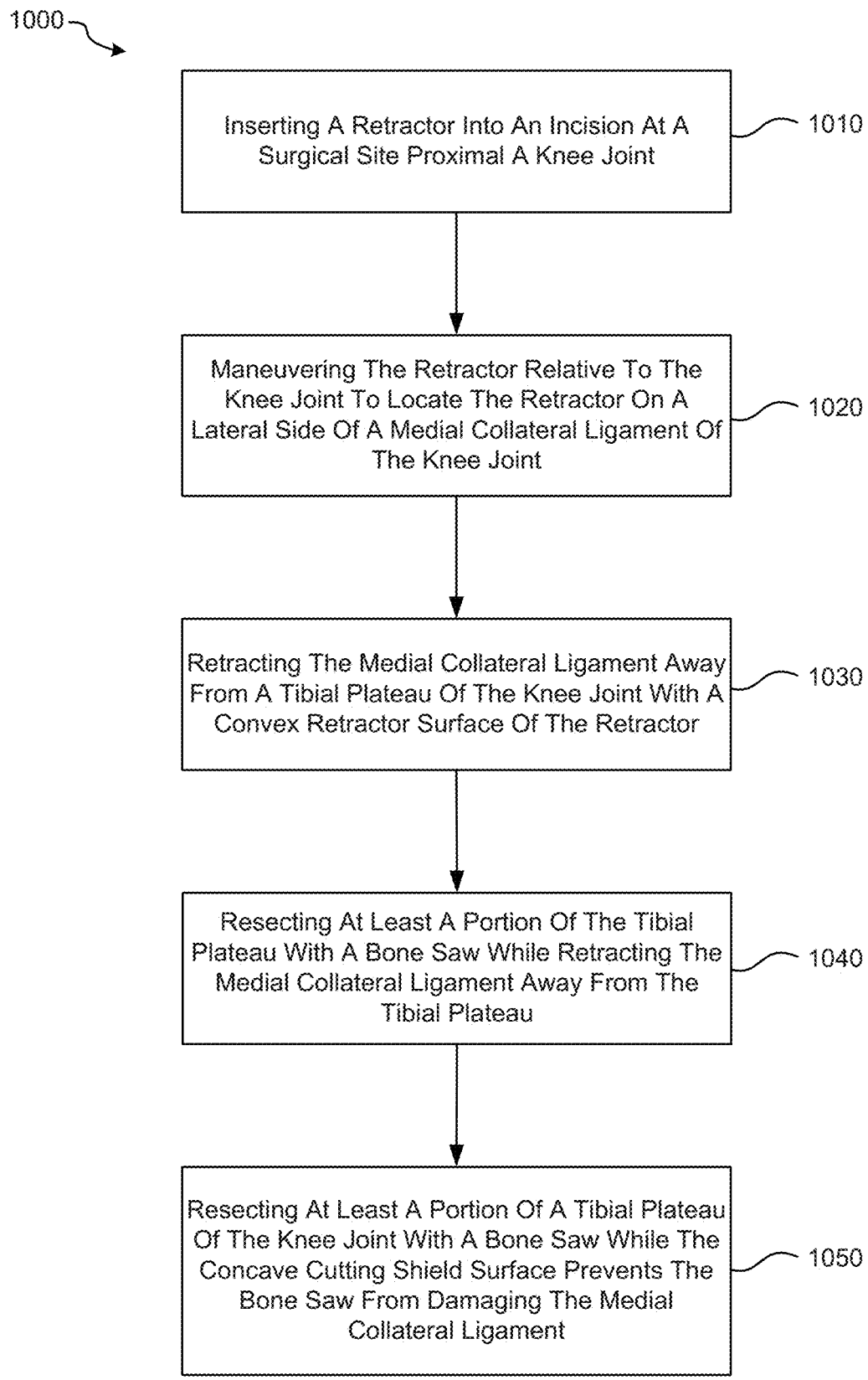
FIG. 10 is a flowchart of a method for retracting a medial collateral ligament with a retractor during a knee joint arthroplasty procedure.

FIG. 10 is a flowchart of a method 1000 for retracting a medial collateral ligament of a knee joint with a retractor 100. The retractor 100 may include a generally arcuate projection having a retractor surface 135 that may be convex and a cutting shield surface 136 that may be concave.

The method 1000 may begin with a step 1010 in which the retractor 100 may be inserted into an incision (not shown) at a surgical site proximal the knee joint.

Once the retractor 100 has been inserted into the incision, the method 1000 may proceed to a step 1020 in which the retractor 100 may be maneuvered relative to the knee joint in order to locate the retractor 100 on a lateral side of the medical collateral ligament.

Once the retractor 100 has been located on the lateral side of the medical collateral ligament, the method 1000 may proceed to a step 1030 in which the surgeon may utilize the retractor surface 135 of the retractor 100 to retract the medial collateral ligament away from a tibial plateau of the knee joint.

Alternatively, or in addition thereto, the method 1000 may proceed to a step 1040 in which a portion of the tibial plateau may be resected with a bone saw while the medial collateral ligament is retracted away from the tibia in order to prevent the bone saw from damaging the medial collateral ligament.

Alternatively, or in addition thereto, the method 1000 may proceed to a step 1050 in which a portion of the tibial plateau may be resected with a bone saw while the cutting shield surface 136 of the retractor 100 directly prevents the bone saw from damaging the medial collateral ligament, and the method 1000 may end.

Thus, as previously discussed, the medial collateral ligament may be protected from damage by the bone saw during the resection procedure. The retractor 100 may protect the medial collateral ligament including: (1) via retraction, which increases a separation distance between the bone saw blade and the medial collateral ligament, thus decreasing the likelihood of damaging the medial collateral ligament; and (2) the cutting shield surface 136 of the retractor 100 may directly shield the medial collateral ligament from the bone saw blade to prevent the bone saw blade from damaging the medial collateral ligament.

Any methods disclosed herein may comprise one or more steps or actions for performing the described method. One or more of the method steps or actions may be omitted from any of the methods disclosed herein. Moreover, any of the method steps or actions may be interchanged with one another. In other words, unless a specific order of steps or actions is required for proper operation of the embodiment, the order and/or use of specific steps or actions may be modified.

It will also be understood that any of the ligament retractor instruments, components, assemblies, systems, and/or methods that are described herein may be mixed and matched in any number of combinations without departing from the spirit or scope of the present disclosure. For example, the retractor 100 of FIGS. 1A-1I may be utilized with the guide rod 200 including any of the hook member 230 embodiments shown in FIGS. 2C-2H for, etc. As another non-limiting example, the hook member 230 may be coupled with the guide projection 150 (instead of the guide rod 200) and the attachment aperture 160 may be formed in the guide rod 200 (instead of the guide projection 150), etc.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles set forth herein.

The phrases "connected to," "coupled to," "engaged with," and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature is able to pass into the other feature. The phrase "substantially equal to" means "equal to," or within about a + or −10% relative variance from one another.

A "curvature" may not only include shapes extending along a curvilinear pathway, but also shapes consisting of a series of rectilinear segments that combine to define larger scale curvature. Thus, for example, a geodesic dome may be said to have a spherical curvature even though the spherical shape is defined by planar segments.

While specific embodiments and applications of the present disclosure have been illustrated and described, it is to be understood that the scope of the appended claims is not limited to the precise configuration and components disclosed herein. Various modifications, changes, and variations which will be apparent to those skilled in the art may be made in the arrangement, operation, and details of the devices, systems, and methods disclosed herein.

What is claimed is:

1. A method for retracting a medial collateral ligament with an assembly comprising a retractor including a retractor coupling feature and a guide rod including a rod coupling feature configured to engage the retractor coupling feature and pivotably couple the guide rod to the retractor, the method comprising:

pivotally coupling the guide rod to the retractor by engaging the rod coupling feature with the retractor coupling feature;

inserting the assembly into an incision at a surgical site proximal a knee joint; and maneuvering the assembly relative to the knee joint and placing the assembly on a lateral side of a medial collateral ligament of the knee joint.

2. The method of claim 1, further comprising:

decoupling the guide rod from the retractor by applying a distally directed force to the guide rod; and removing the guide rod from the knee joint.

3. The method of claim 2, further comprising:

retracting the medial collateral ligament away from a tibial plateau of the knee joint with the retractor.

4. The method of claim 3, further comprising:

resecting at least a portion of the tibial plateau with a bone saw while retracting the medial collateral ligament away from the tibial plateau to prevent damaging the medial collateral ligament with the bone saw.

5. A method for retracting a medial collateral ligament of a knee joint with a retractor comprising a generally arcuate projection having a convex retractor surface, a concave cutting shield surface, and a guide projection extending from the concave cutting shield surface, the method comprising:

inserting the retractor into an incision at a surgical site proximal the knee joint;

maneuvering the retractor relative to the knee joint to locate the convex retractor surface on a lateral side of the medial collateral ligament and the concave cutting shield surface adjacent a tibial plateau of a tibia of the knee joint; and placing the guide projection extending from the concave cutting shield surface on a femur-facing surface of the tibial plateau.

6. The method of claim 5, further comprising:

retracting the medial collateral ligament away from the tibial plateau of the knee joint with the convex retractor surface.

7. The method of claim 6, further comprising:

resecting at least a portion of the tibial plateau with a bone saw while retracting the medial collateral ligament away from the tibial plateau in order to prevent damaging the medial collateral ligament with the bone saw.

8. The method of claim 5, further comprising:

resecting at least a portion of the tibial plateau of the knee joint with a bone saw while the concave cutting shield surface prevents the bone saw from damaging the medial collateral ligament.

9. A method for retracting a medial collateral ligament with an assembly comprising a retractor comprising a retractor coupling feature and a generally arcuate projection having a convex retractor surface and a concave cutting shield surface, and a guide rod comprising a rod coupling feature configured to engage the retractor coupling feature and pivotably couple the guide rod to the retractor, the method comprising:

pivotally coupling the guide rod to the retractor by engaging the rod coupling feature with the retractor coupling feature;

inserting the assembly into an incision at a surgical site proximal a knee joint; and maneuvering the assembly relative to the knee joint to locate the assembly on a lateral side of the medial collateral ligament of the knee joint.

10. The method of claim 9, further comprising:

decoupling the guide rod from the retractor by applying a distally directed force to the guide rod; and removing the guide rod from the knee joint.

11. The method of claim 10, further comprising:

retracting the medial collateral ligament away from a tibial plateau of the knee joint with the retractor.

12. The method of claim 11, further comprising:

resecting at least a portion of the tibial plateau with a bone saw while retracting the medial collateral ligament away from the tibial plateau to prevent damaging the medial collateral ligament with the bone saw.

\* \* \* \* \*